United States Patent [19]

Suzuki et al.

[11] Patent Number: 5,484,924
[45] Date of Patent: Jan. 16, 1996

[54] IMIDAZONAPHTHYRIDINE DERIVATIVES

[75] Inventors: Fumio Suzuki, Mishima; Takeshi Kuroda, Tokushima; Takashi Kawakita, Shizuoka; Shigeto Kitamura, Machida; Haruhiko Manabe, Shizuoka, all of Japan

[73] Assignee: Kyowa Hakko Kogyo Co., Ltd., Tokyo, Japan

[21] Appl. No.: 244,268

[22] PCT Filed: Nov. 24, 1992

[86] PCT No.: PCT/JP92/01532

§ 371 Date: Aug. 31, 1994

§ 102(e) Date: Aug. 31, 1994

[87] PCT Pub. No.: WO93/11127

PCT Pub. Date: Jun. 10, 1993

[30] Foreign Application Priority Data

Nov. 25, 1991 [JP] Japan ................. 3-309108

[51] Int. Cl.⁶ ............................... C07D 471/14
[52] U.S. Cl. .................................... 546/82
[58] Field of Search ........................... 546/82

[56] References Cited

U.S. PATENT DOCUMENTS

| 4,994,468 | 2/1991 | Suzuki et al. | 514/293 |
| 5,364,859 | 11/1994 | Suzuki | 514/293 |

FOREIGN PATENT DOCUMENTS 83595 7/1977 Japan.

Primary Examiner—C. Warren Ivy
Assistant Examiner—Evelyn Huang
Attorney, Agent, or Firm—Fitzpatrick, Cella, Harper & Scinto

[57] ABSTRACT

The present invention relates to novel imidazonaphthyridine derivatives represented by the following formulae:

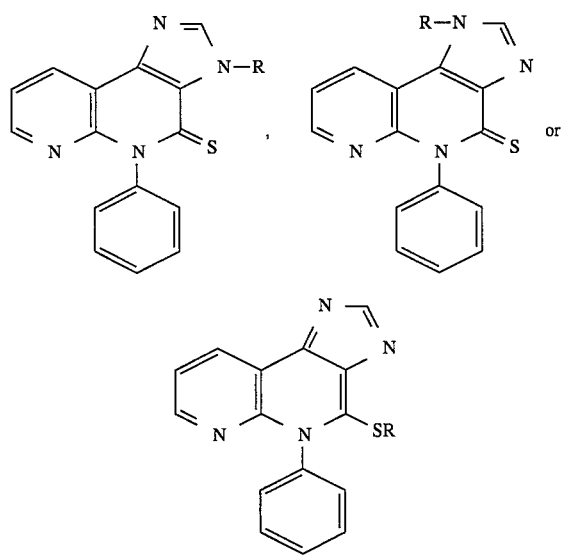

wherein R represents hydrogen, lower alkyl or —$CH_2R^1$ (where $R^1$ represents phenyl or pyridyl) and pharmaceutically acceptable salts thereof.

The compounds exhibit excellent anti-allergic, anti-inflammatory and anti-asthmatic activities.

1 Claim, No Drawings

IMIDAZONAPHTHYRIDINE DERIVATIVES

This application is the National phase of PCT/JP 92/10532 filed on Nov. 24, 1992.

TECHNICAL FIELD

The present invention relates to novel imidazonaphthridine derivatives showing anti-allergic, anti-inflammatory and anti-asthmatic activities.

BACKGROUND ART

U.S. Pat. No. 4,994,468 discloses certain 4-thioimidazo [4,5-c]quinoline derivative showing bronchodilatory and anti-allergic activities. However, 4-thio- or 4-substituted mercaptoimidazo[4,5-c][1,8]naphthyridine derivatives are unknown.

DISCLOSURE OF THE INVENTION

The present invention relates to imidazonaphthridine derivatives represented by Formula (I):

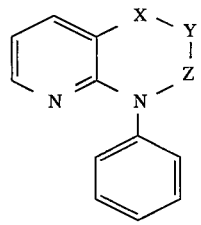

wherein X-Y-Z represents

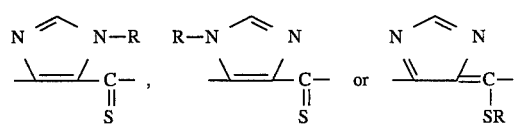

wherein R represents hydrogen, lower alkyl or —$CH_2R^1$ (wherein $R^1$ represents phenyl or pyridyl)] and pharmaceutically acceptable salts thereof.

Compounds (I) wherein R is hydrogen can exist in the form of tautomers, namely Compounds (Ia), (Ia1) and/or (Ia2). All the tautomers are included in the scope of the present invention, and they are collectively referred to as Compound (Ia) in the following description.

pyl, butyl, isobutyl, sec-butyl, tert-butyl, pentyl, neopentyl, and hexyl.

The pharmaceutically acceptable salts of Compounds (I) include acid addition salts, metal salts, ammonium salts, organic amine addition salts, amino-acid addition salts.

As the pharmaceutically acceptable acid addition salts of Compound (I), inorganic acid addition salts such as hydrochloride, sulfate and phosphate, and organic acid addition salts such as acetate, maleate, fumarate, tartrate and citrate may be mentioned. As the pharmaceutically acceptable metal salts, alkali metal salts such as sodium salt and potassium salts, alkaline earth metal salts such as magnesium salt and calcium salt, aluminum salt, and zinc salt may be mentioned. As the pharmaceutically acceptable organic amine addition salts, salts with morpholine and piperidine are mentioned. As the pharmaceutically acceptable amino acid addition salts, salts with lysine, glycine, and phenylalanine may be mentioned.

The processes for preparing Compounds (I) are described below.

In the following processes, when the defined group is changed under the experimental condition or is inappropriate for practicing the processes, the processes can be readily carried out by applying the conventional manner in organic synthetic chemistry, for example, protection of functional groups and elimination of protecting groups.

Compound (I) can be obtained by the following reaction steps.

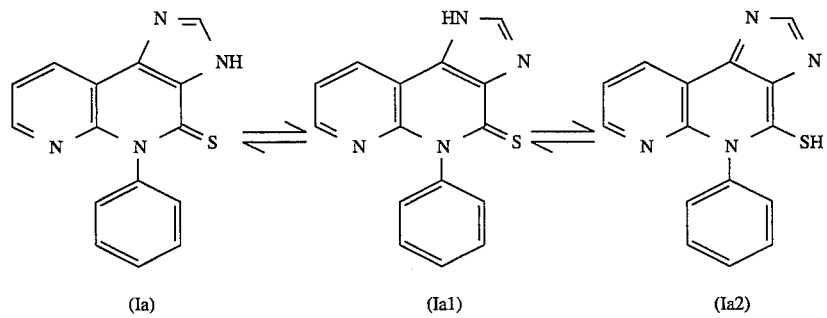

(Ia)  (Ia1)  (Ia2)

In the definitions of the groups in Formula (I), lower alkyl means a straight-chain or branched alkyl group having 1 to 6 carbon atoms, for example, methyl, ethyl, propyl, isopro-

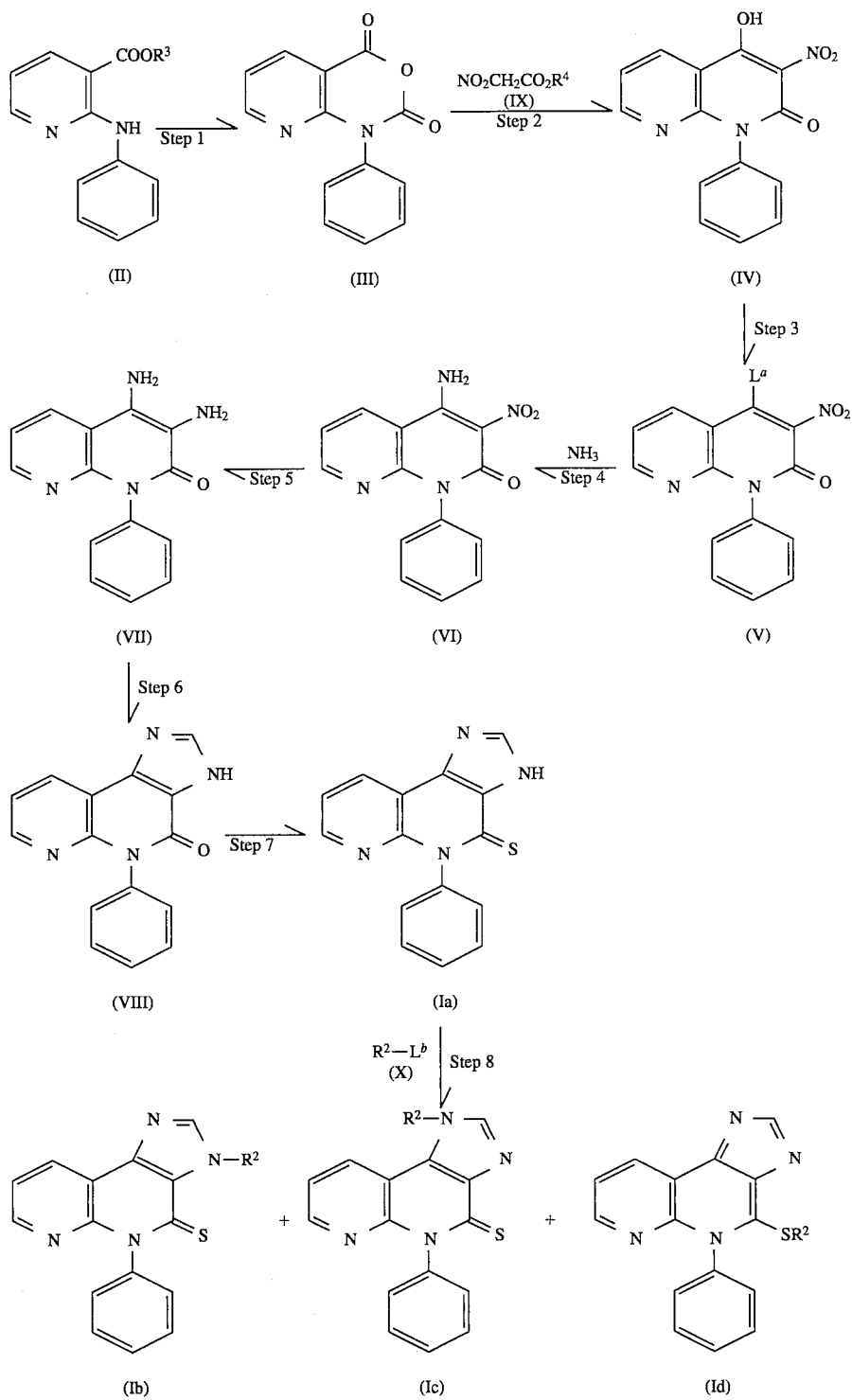

In the formulae, $L^a$ and $L^b$ represents a leaving group; $R^2$ represents the same groups as those defined in R above excluding hydrogen; $R^3$ represents hydrogen or lower alkyl; and $R^4$ represents lower alkyl.

Lower alkyl represented by $R^3$ and $R^4$ means straight-chain and branched alkyl groups having 1 to 6 carbon atoms. Examples of the leaving group represented by $L^a$ and $L^b$ include a halogen atom such as chlorine, bromine and iodine, alkylsulfonyloxy such as methanesulfonyloxy, and arylsulfonyloxy such as phenylsulfonyloxy and p-toluenesulfonyloxy.

The starting Compound (II) can be synthesized according to a known method, as described in J. Org. Chem., 39, 1803 (1974), or by a similar method.

(Step 1)

Compound (III) can be obtained by reacting Compound (II) with phosgene, triphosgene or trichloromethyl chloro formate (TCF), if necessary, in a reaction solvent.

The reaction solvent includes for example, ethers such as tetrahydrofuran and dioxane, hydrocarbons such as toluene and hexane, and halogenated hydrocarbons such as 1,2-dichloroethane and chloroform, etc. These solvents are inert to the reaction and are used alone or in combination. The reaction is carried out at 0° to 200° C. and completed in 5 minutes to 24 hours.

(Step 2)

Compound (IV) can be obtained by reacting Compound (III) with Compound (IX) in the presence of a base, if necessary, in a reaction solvent.

Examples of the base include alkali metal carbonates such as potassium carbonate and sodium carbonate, alkali metal hydrides such as sodium hydride, alkali metal alkoxides such as sodium methoxide and sodium ethoxide, and alkylamines such as triethylamine. The reaction solvent includes ethers such as tetrahydrofuran and dioxane, amides such as dimethylformamide, hydrocarbons such as xylene, toluene, hexane and cyclohexane, and dimethylsulfoxide. These solvents are inert to the reaction and are used alone or in combination. The reaction is carried out at 0° to 300° C. and completed in 10 minutes to 24 hours.

(Step 3)

Compound (Va), which is Compound (V) wherein $L^a$ is sulfonyloxy, can be obtained by reacting Compound (IV) with sulfonyl chloride in the presence or absence of a base and a solvent.

Examples of the base include alkali metal carbonates such as potassium carbonate and sodium carbonate, alkali metal hydrides such as sodium hydride, alkali metal alkoxides such as sodium methoxide and sodium ethoxide, and alkylamines such as triethylamine. The reaction solvent includes ethers such as tetrahydrofuran and dioxane, amides such as dimethylformamide, hydrocarbons such as xylene, toluene, n-hexane and cyclohexane, haloalkanes such as chloroform and carbon tetrachloride, and dimethylsulfoxide. These solvents are inert to the reaction and are used alone or in combination. Examples of sulfonyl chloride include alkylsulfonyl chlorides such as methanesulfonyl chloride, and arylsulfonyl chlorides such as p-toluenesulfonyl chloride. The reaction is carried out at 0° to 100° C. and completed in 5 minutes to 24 hours.

Compound (Vb), i which is Compound (V) wherein $L^a$ is halogen, can be obtained by reacting Compound (IV) with a halogenating agent in the presence or absence of a reaction solvent, if necessary, in the presence of a base.

The same base and solvent as used in the production process of Compound (Va) can be used. The halogenating agents include thionyl chloride, phosphorus oxychloride, phosphorus pentachloride, phosphorus tribromide, etc. The reaction is carried out at 0 to 200° C. and completed in 5 minutes to 24 hours.

(Step 4)

Compound (VI) can be obtained by reacting Compound (V) with ammonia in the presence or absence of a solvent, if necessary, in the presence of a base.

Examples of the base include alkali metal carbonates such as potassium carbonate and sodium carbonate, and alkylamines such as triethylamine. The reaction solvent includes ethers such as tetrahydrofuran and dioxane, amides such as dimethylformamide, hydrocarbons such as xylene, toluene, n-hexane and cyclohexane, haloalkanes such as chloroform and carbon tetrachloride, and dimethylsulfoxide. These solvents are inert to the reaction and are used alone or in combination. The reaction is carried out at 0° to 100° C. and completed in 5 minutes to 24 hours.

(Step 5)

Compound (VII) can be obtained by reducing Compound (VI) in a reaction solvent.

Reduction is carried out, for example, by catalytic reduction using a catalyst such as palladium/carbon and platinum oxide; reduction using a metal such as iron and zinc; and reduction using a metal sulfur derivative such as sodium hydrosulfite.

The reaction solvent includes ethers such as tetrahydrofuran and dioxane, amides such as dimethylformamide, alcohols such as methanol and ethanol, acids such as hydrochloric acid, acetic acid and sulfuric acid, and water. These solvents are inert to the reaction and are used alone or in combination. The reaction is carried out at 0° to 100° C. and completed in 5 minutes to 24 hours.

(Step 6)

Compound (VIII) can be obtained by reacting Compound (VII) with a reactive derivative of formic acid in the presence or absence of a solvent, if necessary, in the presence of an acid.

Examples of the reactive derivative include alkyl orthoformates such as ethyl orthoformate, formamide, and formamidine. The reaction solvent includes hydrocarbons such as toluene and xylene, ethers such as diphenyl ether, glycerol triethyl ether, butyl ether and isoamyl ether, alcohols such as methanol and ethanol, Dowtherm A (Dow Chemical Co.), and hexamethylphosphramide can be used. The acid includes inorganic acids such as hydrochloric acid and sulfuric acid, and organic acids such as acetic acid and p-toluenesulfonic acid. The reaction is carried out at 0° to 250° C. and completed in 5 minutes to 24 hours.

(Step 7)

Compound (Ia) can be obtained by reacting Compound (VIII) with phosphorus pentasulfide or Lawesson's reagent (1,3-dithia-2,4-diphosphatan-2,4-disulfide) in the presence of a reaction solvent.

When Lawesson's reagent is used as the reaction solvent, hydrocarbons such as toluene and xylene are preferably used. When phosphorus pentasulfide is used as the reaction solvent, pyridine or the like is preferably used. The reaction is carried out at 0° to 200° C. and completed in 5 minutes to 24 hours.

(Step 8)

Compounds (I) wherein R is a group other than hydrogen, namely Compounds (Ib), (Ic) and (Id), can be obtained by reacting Compound (Ia) with Compound (X) in a reaction solvent in the presence of a base.

Examples of the base include alkali metal carbonates such as potassium carbonate and sodium carbonate, alkali metal hydrides such as sodium hydride, and alkali metal alkoxides such as sodium methoxide and sodium ethoxide. The reaction solvent includes ethers such as tetrahydrofuran and dioxane, amides such as dimethylformamide, alcohols such as methanol and ethanol, and dimethylsulfoxide. These solvents are inert to the reaction and are used alone or in combination. The reaction is carried out at 0° to 100° C. and completed in 5 minutes to 24 hours.

The intermediates and the desired compounds in the processes described above can be isolated and purified by purification methods conventionally used in organic synthetic chemistry, for example, filtration, extraction, washing, drying, concentration, recrystallization, and various kinds of chromatography. The intermediates can also be subjected to the subsequent reaction without purification.

In the case where a salt of Compound (I) is desired and it is produced in the form of the desired salt, it can be subjected to purification as such. In the case where Compound (I) is produced in the free state and its salt is desired, Compound (I) is dissolved or suspended in a suitable solvent, followed by addition of an acid or base to form a salt.

Compound (I) and pharmaceutically acceptable salts thereof may exist in the form of adducts with water or various solvents, which are also within the scope of the present invention.

Specific examples of compounds of the present invention are shown in Tables 1-1 and 1-2.

TABLE 1-1

| Compound No. | —R |
|---|---|
| 1 | —H |
| 2 | —CH$_2$—(phenyl) |
| 4 | —CH$_2$CH(CH$_3$)$_2$ |
| 5 | —CH$_2$—(pyridyl) |
| 6 | —CH$_3$ |

TABLE 1-2

| Compound No. | —R |
|---|---|
| 3 | —CH$_2$—(phenyl) |
| 7 | —CH$_3$ |

The pharmacological activity of Compound (I) is shown below by a test example.

Test Example 1

Effect on passive Shultz-Dale reaction (broncho-dilative activity)

Male Hartley guinea pigs weighing 350 to 500 g were passively sensitized by intraperitoneal injection of rabbit anti-OA serum prepared in advance by the method of Koda et al. [Folia Pharmacol., Japon 66, 237, (1970)]. After 24 hours, tracheae were removed from guinea pigs and used for experiment. The zig-zag strips of the tracheae were prepared by the method of Emmerson and Mackay [J. Pharm. Pharmacol., 31, 798, (1979)]. The strips were suspended in Krebs-Henseleit solution at 37° C. under aeration of a mixed gas of 95% oxygen and 5% carbon dioxide, and equilibrated for one hour. Then, antigen (egg white albumin) was introduced in the solution (final concentration; 1 µg/ml), and the contraction was measured by isotonic transducer (TD-112s, made by Nihon Kohden K. K., Japan) and recorded on a recorder (Type 3066, made by Yokogawa-Hokushin Denki, K. K. Japan). After the contraction curves reached a plateau, the test compounds were successively added in order to get cumulative concentration-relaxation curves. The concentration of 50% relaxation rate (IC$_{50}$) was calculated from the regression line, which was obtained from the cumulative concentration-relaxation curves.

The results are shown in Table 2.

TABLE 2

| Compound No. | Broncho-dilative Activity (IC$_{50}$: µM) |
|---|---|
| Compound 1 | 4.8 |

Compound (I) and pharmaceutically acceptable salts thereof can be administered as they are, or in the form of various pharmaceutical compositions. The pharmaceutical compositions in accordance with the present invention can be prepared by uniformly mixing an effective amount of Compound (I) or a pharmaceutically acceptable salt thereof, as an active ingredient, with a pharmaceutically acceptable carrier. It is desired that such pharmaceutical compositions are prepared in a single dose unit suitable for oral administration for injection.

In preparing a pharmaceutical composition for oral administration, any pharmaceutically acceptable carriers can be used. For example, liquid preparations for oral administration such as suspensions and syrup can be prepared using water, sugars such as sucrose, sorbitol and fructose, glycols such as polyethylene glycol and propylene glycol, oils such as sesame oil, olive oil and soybean oil, preservatives such as p-hydroxybenzoic acid esters, and flavors such as strawberry flavor and peppermint, etc. Tablets and capsules are the most useful oral unit dose forms since their administration is convenient. In preparing tablets and capsules, solid pharmaceutical carriers are used. Powders, pills, capsules and tablets can be prepared using excipients such as lactose, glucose, sucrose and mannitol, disintegrators such as starch and sodium alginate, lubricants such as magnesium stearate and talc, binders such as polyvinyl, alcohol, hydroxypropyl cellulose and gelatin, surfactants such as fatty acid esters, and plasticizers such as glycerine, etc.

A solution for injection can be prepared using carriers such as distilled water, a saline solution, a glucose solution, and a mixture of a saline solution and a glucose solution.

The effective dose and the administration schedule of Compound (I) and pharmaceutically acceptable salts thereof vary depending on the mode of administration, the age, body weight and conditions of a patient, etc. It is generally preferred to administer Compound (I) or a pharmaceutically acceptable salt thereof to a patient in a daily dose of 1 to 1000 mg in 1 to 4 parts.

Furthermore, Compound (I) can be administered by inhalation in the form of an aerosol, finely pulverized powders, or spray solution. In the case of aerosol administration, the compounds are dissolved in an appropriate pharmaceutically acceptable solvent such as ethyl alcohol or a combination of miscible solvents, and then mixed with a pharmaceutically acceptable propellant.

Certain embodiments of the present invention are illustrated in the following examples, reference examples and preparation examples.

EXAMPLE 1

5-Phenyl-3H-imidazo[4,5-c][1,8]naphthyridin-4(5H)-thione (Compound 1)

Into 40 ml of pyridine were suspended 2.0 g (7.6 mmol) of Compound (e) obtained in Reference Example 5 and 2.8 g (12 mmol) of phosphorus pentasulfite, and the suspension was heated under reflux for 2 hours. The resulting solution was cooled to room temperature, and water was added thereto to form a precipitate. The precipitate was collected by filtration and recrystallized from dimethylformamide-water to give 1.8 g (85%) of Compound 1 as yellow crystals.

Melting point: >300° C.

Elemental analysis (%): $C_{15}H_{10}N_4S \cdot 0.4H_2O$ Calcd.; C 63.10, H 3.81, N 19.62 Found; C 63.18, H 3.33, N 19.31

IR (KBr) ν max (cm$^{-1}$): 3362

$^1$H-NMR (d$_6$-DMSD) δ (ppm): 13.63 (1H, br s), 8.65(1H, dd, J=8, 2 Hz), 8.47– 8.50(2H, m), 7.40–7.60 (4H, m), 7.27(2H, d, J=7 Hz)

MS m/e: 278 (M$^+$)

EXAMPLE 2

3-Benzyl-5-phenyl-3H-imidazo[4,5-c][1,8]naphthyridin-4(5H)-thione (Compound 2)
4-Benzylmercapto-5-phenylimidazo[4,5-c][1,8]naphthyridine (Compound 3)

Into 30 ml of dimethylformamide was dissolved 0.79 g (2.5 mmol) of Compound 1 obtained in Example 1. Furthermore, 0.13 g (3.4 mmol) of 60% sodium hydride was added thereto with stirring at room temperature. The mixture was stirred for 1 hour. Then, 0.41 ml (3.4 mmol) of benzyl bromide was added thereto, followed by further stirring for 1 hour. The mixture was cooled with ice and then water was added thereto. The precipitated solid was collected by filtration. The solid was dried, dissolved into chloroform and purified by silica gel column chromatography (eluent: chloroform) to give 0.25 g (24%) of Compound (II) as the first fractions and 0.40 g (38%) of Compound 3 as the second fractions.

Compound 2:

$^1$H-NMR (CDCl$_3$) δ (ppm): 8.74(1H, dd, J=8, 2 Hz), 8.49(1H, dd, J=6, 2 Hz), 8.03(1H, s), 7.20–7.70(11H, m), 6.32(2H, s)

Melting point: 224°–226° C.

Elemental analysis (%): $C_{22}H_{16}N_4S \cdot 0.3H_2O$ Calcd.; C 70.68, H 4.48, N 14.99 Found; C 70.73, H 4.13, N 14.95

IR(KBr) ν max(cm$^{-1}$): 1619, 1580, 1520

MS m/e: 368 (M$^+$)

Compound 3:

$^1$H-NMR (CDCl$_3$) δ (ppm): 9.13(1H, dd, J=8, 1 Hz), 8.59–8.63(2H, m), 7.50–7.65(4H, m), 7.15–7.35(7H, m), 5.45(2H, s)

Melting point: 198°–203° C.

Elemental analysis (%): $C_{22}H_{16}N_4S \cdot 0.1H_2O$ Calcd.; C 71.37, H 4.41, N 15.13 Found; C 71.24, H 4.17, N 15.11

IR (KBr) ν max (Cm$^{-1}$): 1574, 1510

MS m/e: 368 (M$^+$) 277

EXAMPLE 3

3-(2-Methylpropyl)-5-phenyl-3H-imidazo[4,5-c][1,8]naphthyridin-4(15H)-thione (Compound 4)

The same procedure as in Example 2 was repeated except that isobutyl iodide was used instead of benzyl bromide to obtain Compound 4 (yield: 27%).

$^1$H-NMR (CDCl$_3$) δ (ppm): 8.69(1H, dd, J=8, 2 Hz), 8.48(1H, dd, J=6, 2 Hz), 7.97(1H, s), 7.50–7.70(3H, m), 7.20–7.40(3H, m), 4.65(2H, d, J=7 Hz), 2.30–2.50(1H, m), 0.95(6H, d, J=7 Hz)

Melting point: 167°–169° C.

Elemental analysis (%): $C_{19}H_{18}N_4S$ Calcd.; C 68.24, H 5.42, N 16.75 Found; C 70.62, H 5.22, N 17.34

IR(KBr) ν max(cm$^{-1}$): 1619, 1592, 1520

MS m/e: 335 (M$^+$+1), 279

EXAMPLE 4

3-(3-Pyridylmethyl)-5-phenyl-3H-imidazo[4,5-c][1,8]naphthyridin-4(5H)-thione (Compound 5)

The same procedure as in Example 2 was repeated except that picolyl chloride was used instead of benzyl bromide to obtain Compound 5 (yield: 48%).

$^1$H-NMR (CDCl$_3$) δ (ppm): 8.71(1H, dd, J=8, 2 Hz), 8.45–8.60(3H, m), 8.09(1H, s), 8.45–8.70(4H, m), 7.15–7.40(4H, m), 6.33(2H, s)

Melting point: 222°–224° C.

Elemental analysis (%): $C_{21}H_{15}N_5S$ Calcd.; C 68.27, H 4.09, N 18.96 Found; C 68.37, H 3.80, N 18.71

IR(KBr) ν max(cm$^{-1}$): 1616, 1585, 1520

MS m/e: 369 (M$^+$), 277

EXAMPLE 5

3-Methyl-5-phenyl-3H-imidazo[4,5-c][1,8]naphthyridin-4(5H)thione (Compound 6)
4-Methylmercapto-5-phenylimidazo [4,5-c][1,8]naphthyridine (Compound 7)

The same procedure as in Example 2 was repeated except that methyl iodide was used instead of benzyl bromide to obtain Compound 6 (yield: 37%) and Compound 7 (yield: 10%).

Compound 6:

$^1$H-NMR (CDCl$_3$) δ (ppm): 8.65(1H, dd, J=8, 2 Hz), 8.46(1H, dd, J=6, 2 Hz), 7.97(1H, s), 7.45–7.65(3H, m), 7.15–7.35(3H, m), 4.39(3H, s)

Melting point: 279°–280° C.

Elemental analysis (%): $C_{16}H_{12}N_4S$ Calcd.; C 65.73, H 4.14, N 19.16 Found; C 65.64, H 3.99, N 19.05

IR(KBr) ν max(cm$^{-1}$): 1610, 1588, 1522

MS m/e: 292 (M$^+$)

Compound 7:

$^1$H-NMR (CDCl$_3$) δ (ppm): 9.02(1H, dd, J=8, 2 Hz), 8.59(1H, dd, J=6, 2 Hz), 8.53(1H, s), 7.60–7.70(3H, m), 7.52(1H, dd, J=8, 6 Hz), 7.30–7.40(2H, m), 3.38(3H, s)

Melting point: 234° C.

IR(KBr) ν max(cm$^{-1}$): 1579, 1516

MS m/e: 292 (M$^+$), 245

Reference Example 1

1-Phenyl-2H-pyrido [2,3-d][1,3]oxadin-2,4(1H)-dione (Compound a)

Into a mixture of 70 ml of 1,2-dichloroethane and 7 ml of dioxane was dissolved 7.0 g (0.031 mol) of methyl 2-anilinonicotinate [J. Org. Chem., 39, 1803 (1974)]. After 11 ml (0.092 mol) of trichloromethyl chloroformate was added dropwise to the solution with stirring at 60° C. Then, reaction mixture was heated under reflux for 3 hours. After slight cooling, 0.25 g of activated carbon was added thereto, and the mixture was heated under reflux in a nitrogen flow for 30 minutes. After being cooled to room temperature, the mixture was filtered and concentrated, then the precipitated crystals were recrystallized from methylene chloride/isopropyl ether to give 6.5 g (87%) of Compound (a) as colorless crystals.

Melting point: 196°–198° C.

Elemental analysis (%): $C_{13}H_8N_2S$ Calcd.; C 65.00, H 3.36, N 11.66 Found; C 65.11, H 3.22, N 11.48

IR(KBr) ν max (cm$^{-1}$): 1791, 1727, 1584

$^1$H-NMR (CDCl$_3$) δ (ppm): 8.58(1H, dd, J=5, 2 Hz), 8.48(1H, dd, J=8, 2 Hz), 7.51–7.63(3H, m), 7.33–7.38(2H, m), 7.29(1H, dd, J=8, 5 Hz )

MS m/e: 240 (M$^+$), 196, 168

Reference Example 2

4-Hydroxy-3-nitro-1-phenyl-1,8-naphthyridin-2(1H)-one (Compound b)

Into 25 ml of N,N-dimethylacetamide was dissolved 1.9 ml (0.020 mol) of ethyl nitroacetate, and 0.80 g (0.020 mol) of 60% sodium hydride was added thereto under ice cooling. After evolution of hydrogen ceased, 4.0 g (0.017 mol) of Compound (a) obtained in Reference Example 1 were added thereto, and the mixture was slowly heated and stirred at 100° C. for 30 minutes. The solvent was distilled off under reduced pressure and 200 ml of water was added thereto. The aqueous layer was washed with ethyl acetate, and made acidic with concentrated hydrochloric acid. The precipitated crystals were collected by filtration. The crystals obtained were recrystallized from isopropyl alcohol/ethanol to give 3.6 g (yield: 77%) of Compound (b) as light yellow needles.

Melting point: 296°–298° C.

Elemental analysis (%): $C_{14}H_9N_4S$ Calcd.; C 59.37, H 3.20, N 14.84 Found; C 59.57, H 2.99, N 14.68

IR(KBr) ν max (cm$^{-1}$): 1682, 1587, 1410

$^1$H-NMR (d$_6$-DMSO) δ (ppm): 8.51(1H, dd, J=8, 2 Hz), 8.48(1H, dd, J=4, 2 Hz), 7.41–7.54(3H, m), 7.26–7.36(3H, m)

MS m/e: 283 (M$^+$), 282, 265, 77

Reference Example 3

4-Chloro-3-nitro-1-phenyl-1,8-naphthyridin-2(1H)-one (Compound c)

Into 50 ml (0.54 mol) of phosphorus oxychloride was suspended 10 g (0.038 mol) of Compound (b) obtained in Reference Example 2, and the suspension was heated at 100° C. for 1 hour. The solvent was distilled off under reduced pressure, and 4N sodium hydroxide solution was added under ice cooling for neutralization. The precipitated crystals were collected by filtration to give 5.2 g (49%) of Compound (c) as white crystals.

Melting point (solvent for recrystallization): 228°–232° C. (ethyl acetate-n-hexane)

Elemental analysis (%): $C_{14}H_8NCl_3O_3$ Calcd.; C 55.74, H 2.21, N 13.63 Found; C 55.91, H 2.68, N 13.97

IR(KBr) λ max(cm$^{-1}$): 1667, 1587, 1547

$^1$H-NMR (CDCl$_3$) δ (ppm): 8.62(1H, dd, J=4, 2 Hz), 8.44(1H, dd, J=8, 2 Hz), 8.50–8.65(3H, m), 7.40(1H, dd, J=8, 4 Hz), 7.25–7.33(2H, m)

MS m/e: 300, 302 (M$^+$)

Reference Example 4

4-Amino-3-nitro-1-phenyl-1,8-naphthyridin-2(1H)-one (Compound d)

Into 60 ml of tetrahydrofuran was dissolved 1.8 g (6.0 mmol) of Compound (c) obtained in Reference Example 3, and then 3.6 ml (60 mmol) of 28% aqueous solution of ammonium water was added thereto, followed by stirring at room temperature for 12 hours. The solvent was distilled off under reduced pressure and water was added to the residue. The precipitated crystals were collected by filtration, dried and then recrystallized from dimethylformamide/water, to give 1.5 g (86%) of Compound (d) as light yellow crystals.

Melting point: >300° C.

Elemental analysis (%): $C_{14}H_{10}ClN_4O_3$ Calcd.; C 59.57, H 3.57, N 19.85 Found; C 59.59, H 3.61, N 19.71

IR(KBr) ν max(cm$^{-1}$): 1623

$^1$H-NMR (CDCl$_3$) δ (ppm): 8.79(1H, dd, J=9, 2 Hz), 8.44–8.51(3H, m), 7.23–7.50(6H, m)

MS m/e: 282 (M$^+$)

Reference Example 5

5-Phenyl-3H-imidazo[4,5-c][1,8]-naphthyridin-4(5H)-one (Compound e)

Into a solvent mixture of 10 ml of ethanol and 10 ml of water was suspended 1.7 g (4.0 mmol) of Compound (d) obtained in Reference Example 4, and 2.8 g (16 mmol) of sodium hydrosulfite was added thereto, followed by stirring at an outer temperature of 100° C. for 10 minutes. The resulting solution was cooled and then filtered. The obtained crystals were washed with water. The crystals were then dried, and 8.0 ml (48 mmol) of ethyl orthoformate were added thereto. The mixture was stirred at 130° C. for 1 hour. The resulting solution was cooled, and 30 ml of isopropyl ether was added thereto. The resulting mixture was filtered, and the obtained crystals were recrystallized from dimethylformamide/water to give 0.61 g (yield: 58%) of Compound (e) as white crystals.

Melting point: >300° C.

Elemental analysis (%): $C_{15}H_{10}N_4O \cdot 0.2H_2O$ Calcd.; C 67.76, H 3.94, N 21.07 Found; C 67.92, H 3.45, N 21.10

IR (KBr) ν max(cm$^{-1}$): 1668, 1583, 1423

$^1$H-NMR (d$_6$-DMSO) δ (ppm): 13.84(1H, br.s), 8.50(1H, dd, J=8, 2 Hz), 8.33–8.36(2H, m), 7.42–7.58(3H, m), 7.22–7.38(3H, m)

MS m/e: 262 (M$^+$), 261

Preparation Example 1: Tablet

A tablet having the following composition is prepared in a conventional manner.

| Compound 1 | 100 mg |
| Lactose | 60 mg |
| Potato starch | 30 mg |
| Polyvinyl alcohol | 2 mg |
| Magnesium stearate | 1 mg |
| Tar pigment | trace |

Preparation Example 2: Powder

Powder having the following composition is prepared in a conventional manner.

| Compound 1 | 100 mg |
| Lactose | 300 mg |

Preparation Example 3: Syrup

Syrup having the following composition is prepared in a conventional manner.

| Compound 1 | 100 mg |
| Refined sugar | 30 g |
| Ethyl p-hydroxybenzoate | 40 mg |
| Propyl p-hydroxybenzoate | 10 mg |
| Strawberry flavor | 0.1 ml |

Water is added to the composition to make the total volume 100 ml.

Industrial Availability

With the use of the imidazonaphthridine derivative of the present invention, a pharmaceutical composition which exhibits excellent anti-inflammatory, anti-allergic and anti-asthmatic activities is provided.

What is claimed is:

1. An imidazonaphthyridine derivative represented by Formula (I):

wherein X-Y-Z represents
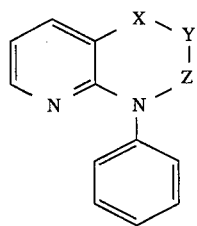
(I) 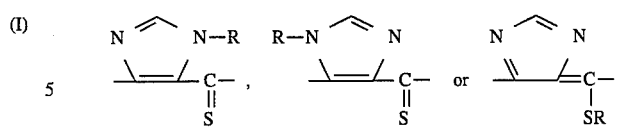
wherein R represents hydrogen, lower alkyl or —CH$_2$R$^1$ (where R$^1$ represents phenyl or pyridyl) and pharmaceutically acceptable salts thereof.
* * * * *